(12) United States Patent
Song

(10) Patent No.: US 8,226,662 B2
(45) Date of Patent: Jul. 24, 2012

(54) RECHARGEABLE TYPE CALLUS REMOVAL INSTRUMENT

(76) Inventor: Jae Hyun Song, Gyeonggi-do (KR)

(*) Notice: Subject to any disclaimer, the term of this patent is extended or adjusted under 35 U.S.C. 154(b) by 257 days.

(21) Appl. No.: 12/676,979

(22) PCT Filed: Sep. 10, 2008

(86) PCT No.: PCT/KR2008/005320
§ 371 (c)(1),
(2), (4) Date: Mar. 8, 2010

(87) PCT Pub. No.: WO2009/038305
PCT Pub. Date: Mar. 26, 2009

(65) Prior Publication Data
US 2010/0326456 A1 Dec. 30, 2010

(30) Foreign Application Priority Data
Sep. 20, 2007 (KR) .......... 10-2007-0095940

(51) Int. Cl.
*A61B 17/50* (2006.01)
(52) U.S. Cl. .......... 606/131; 132/76.4; 604/290
(58) Field of Classification Search .......... 606/131, 606/133, 132; 604/289, 290; 132/73.6, 76.4
See application file for complete search history.

(56) References Cited

U.S. PATENT DOCUMENTS

| 6,178,970 B1 | 1/2001 | Purifoy et al. |
| 6,523,546 B2 | 2/2003 | Jo |
| 7,581,545 B1 * | 9/2009 | Moldawski et al. .......... 132/76.4 |
| 2007/0225732 A1 | 9/2007 | Cho |

FOREIGN PATENT DOCUMENTS

| KR | 20-0385512 Y1 | 5/2005 |
| KR | 10-2005-0105061 A | 11/2005 |

* cited by examiner

*Primary Examiner* — Victor Nguyen
(74) *Attorney, Agent, or Firm* — Duane Morris LLP; J. Rodman Steele, Jr.; Gregory M. Lefkowitz

(57) ABSTRACT

A rechargeable type callus removal instrument is disclosed, that includes a main body having a flaring tube shape with one side opened. The instrument can include a callus storage fitted around the motor shaft of an internal motor that rotates with rotation of the motor shaft, thereby collecting calluses separated from a user's foot therein. A filing cap can cover an upper surface of the callus storage for removing calluses on the user's foot while rotating with the callus storage in contact with a callus surface of the foot. A guide member can be included to assist with forming an exterior barrier such that the calluses being removed by the filing cap are collected in the callus storage without scattering about to the outside. The callus removal instrument enables callus removal using a rotational force of a motor through electric recharging with an improved portability while preventing water infiltration.

14 Claims, 8 Drawing Sheets

[Figure 1]
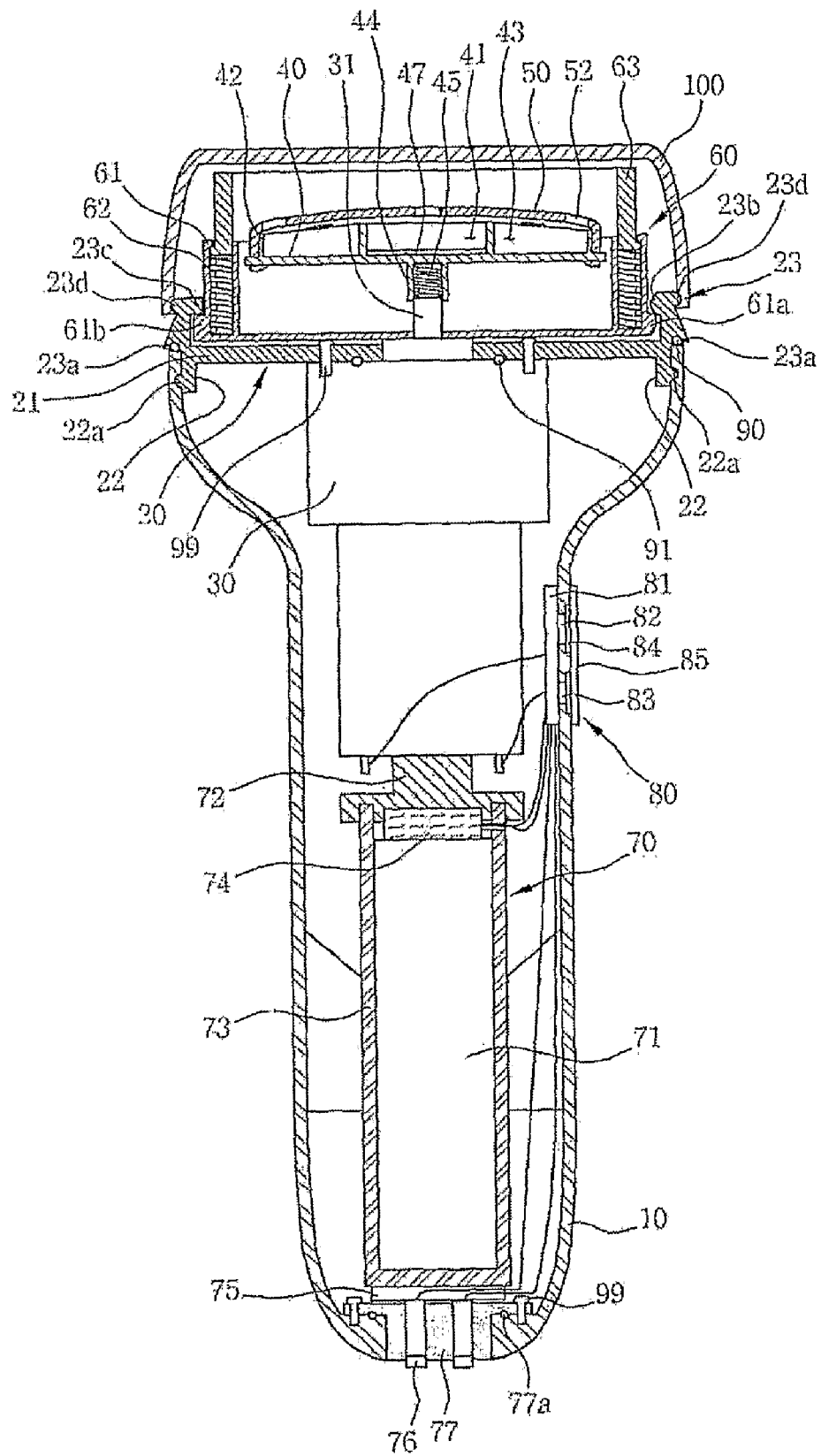

[Figure 2]
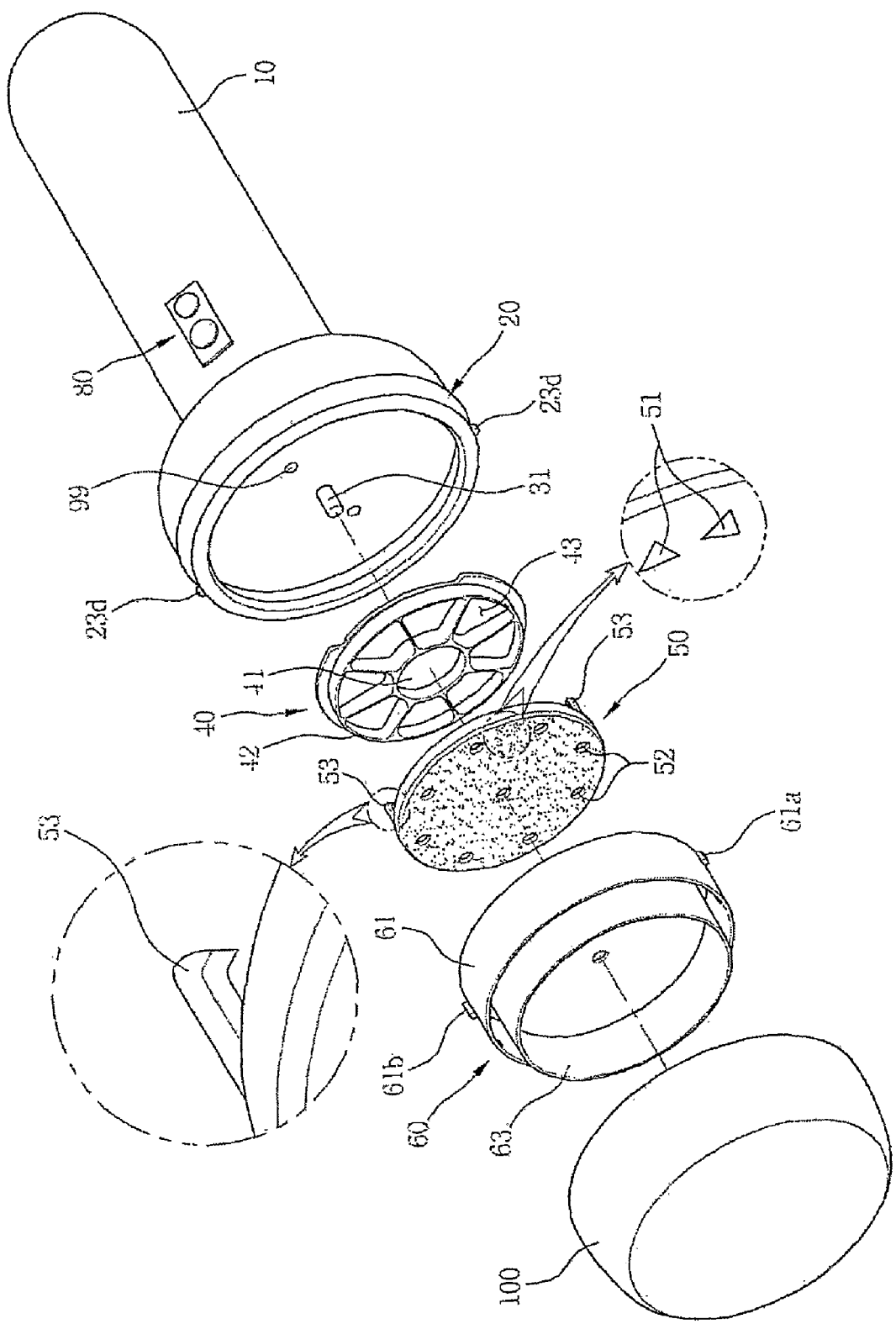

[Figure 3]
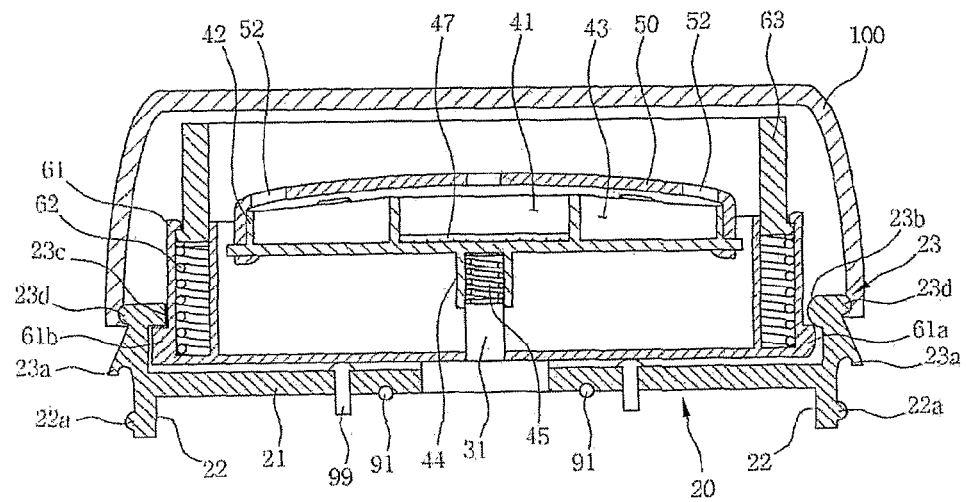
[Figure 4]
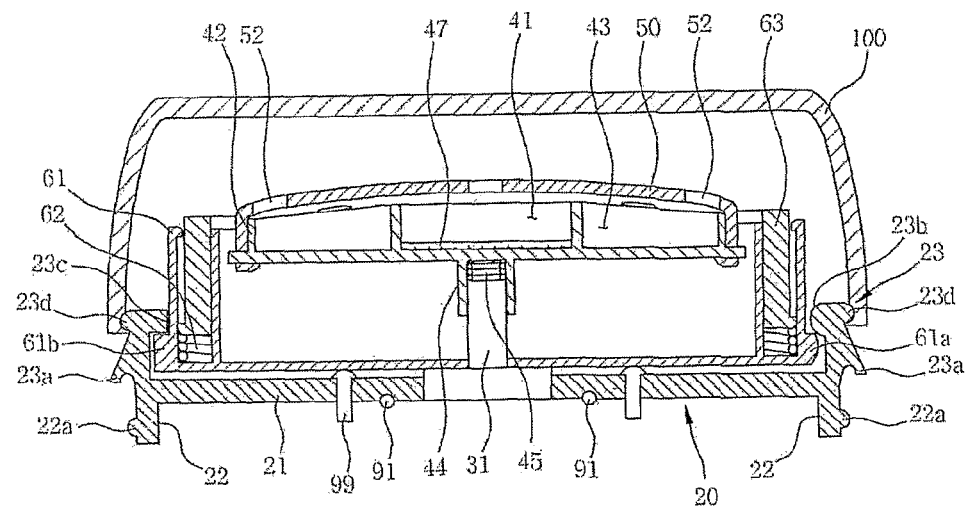

[Figure 5]
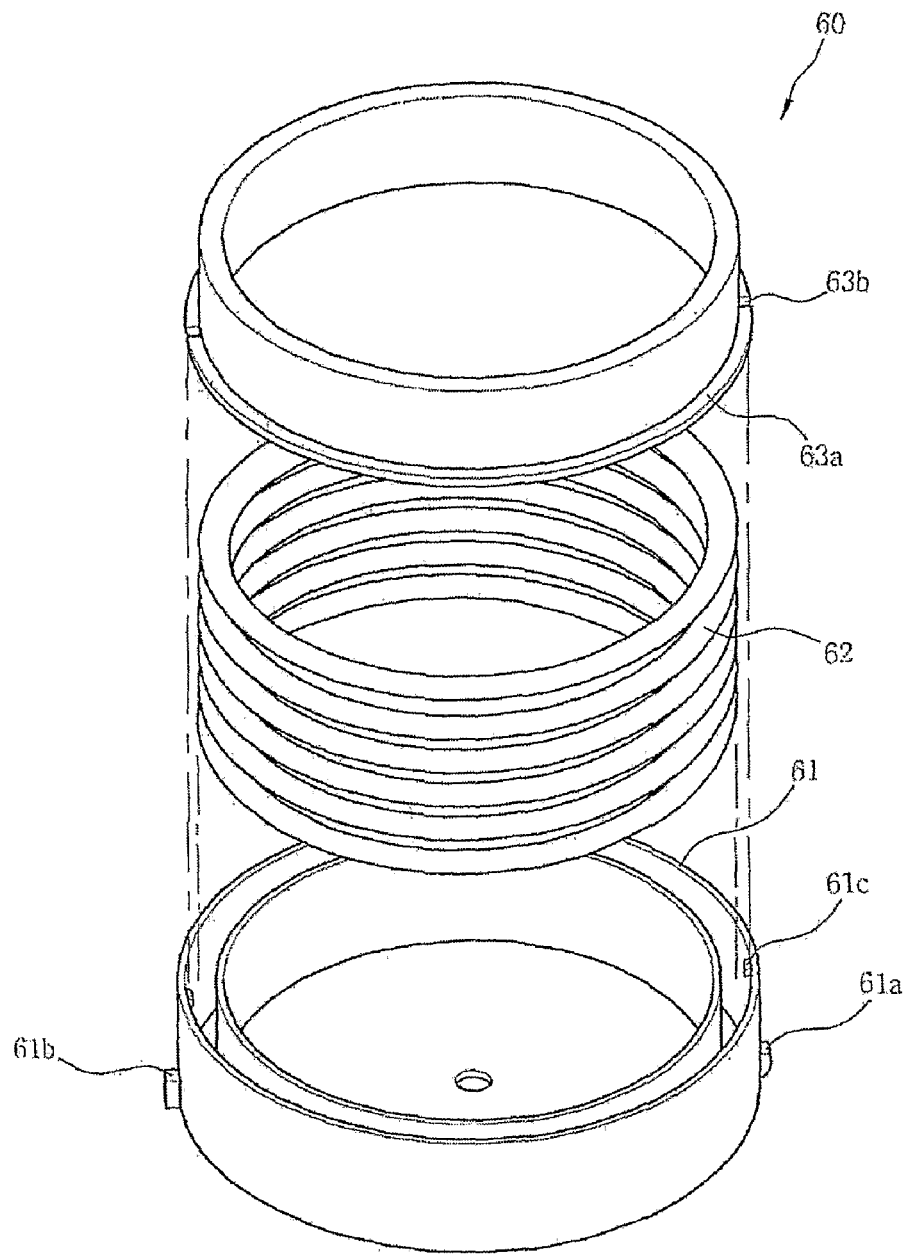

[Figure 6]
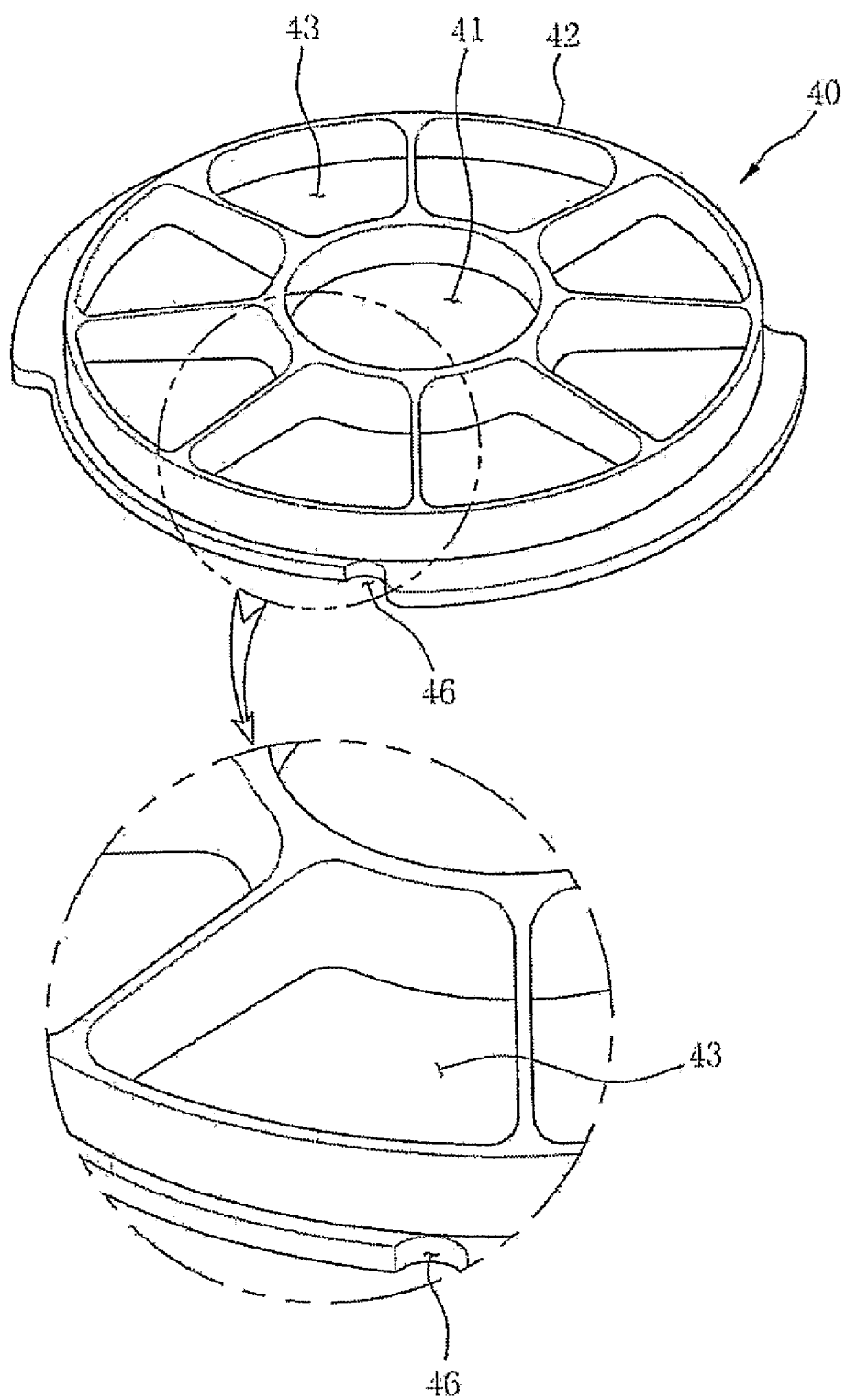

[Figure 7]
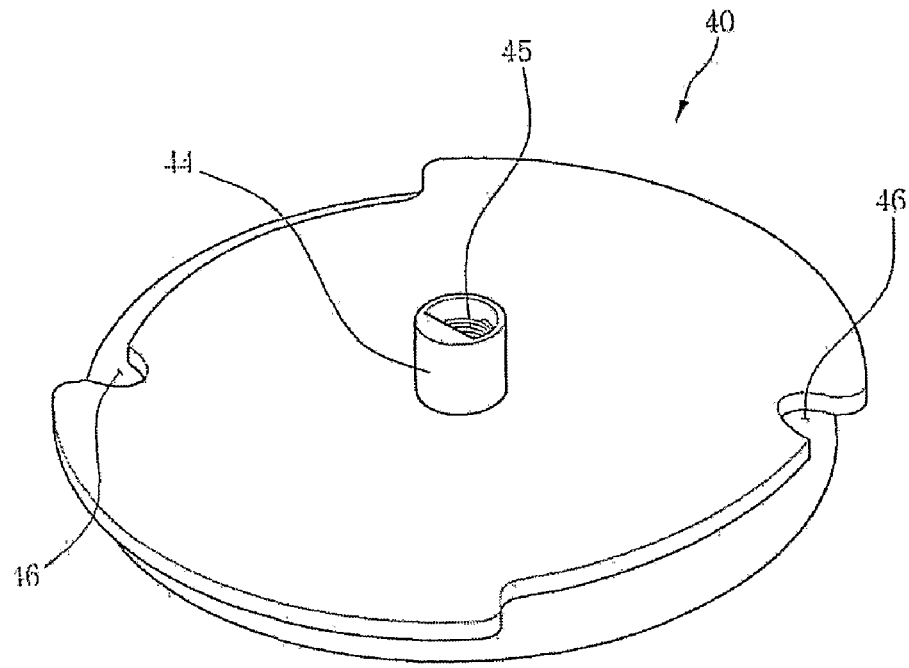
[Figure 8]
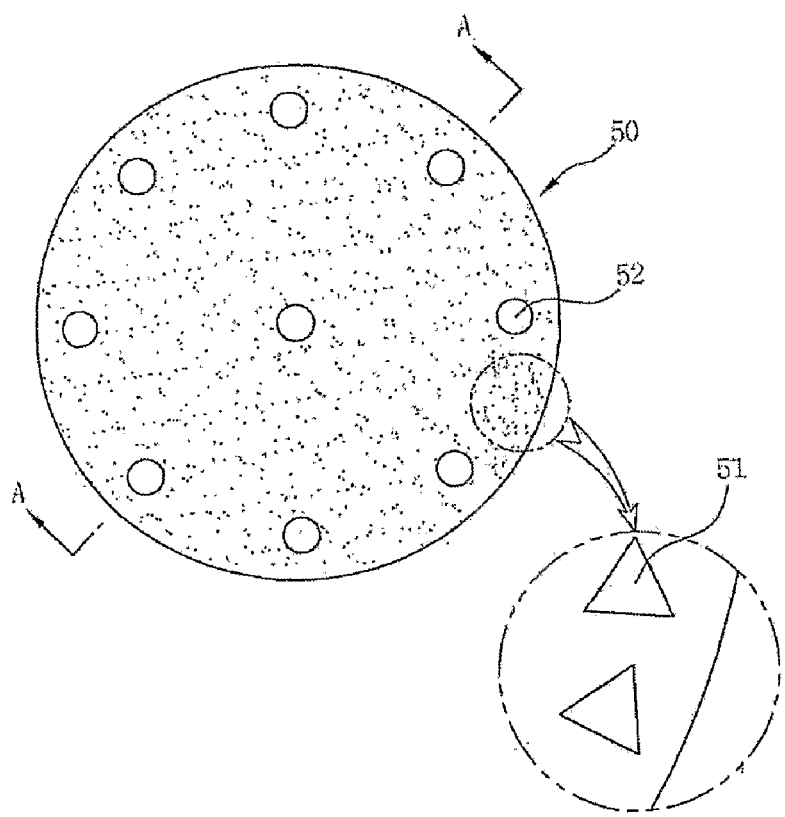

[Figure 9]
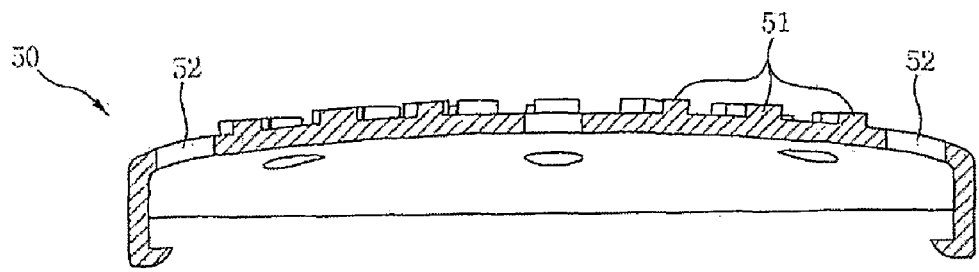
[Figure 10]
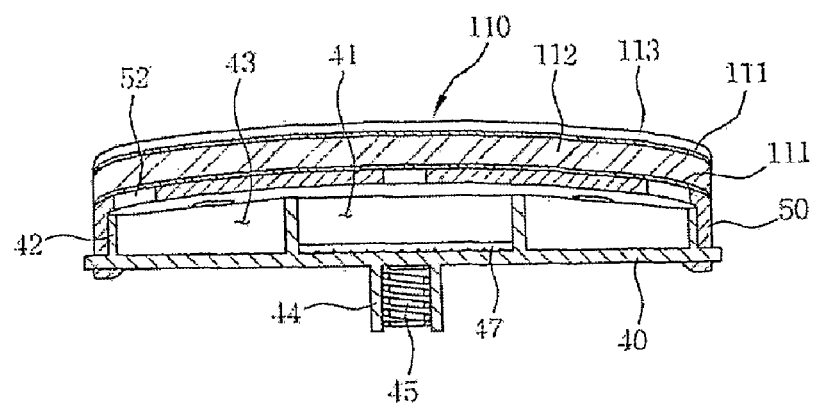
[Figure 11]
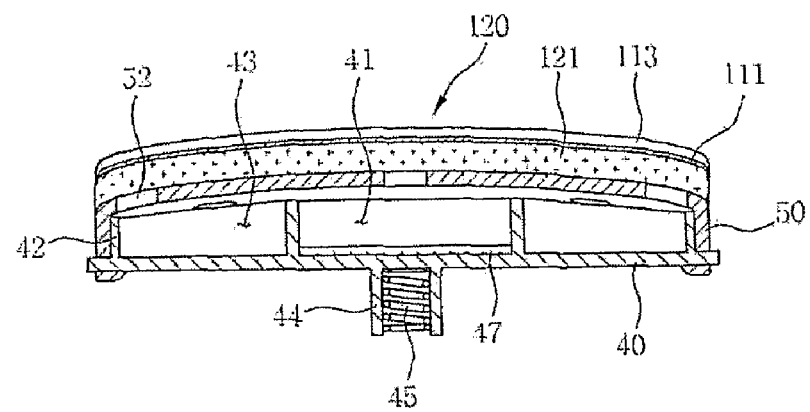

[Figure 12]
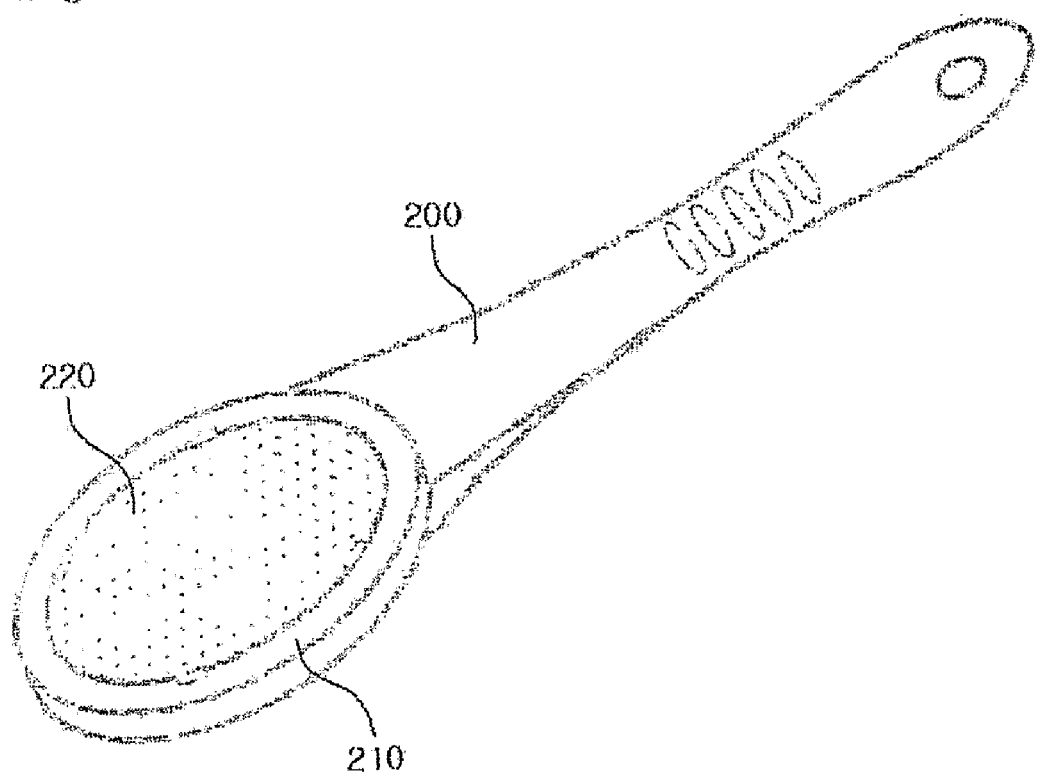

RECHARGEABLE TYPE CALLUS REMOVAL INSTRUMENT

CROSS-REFERENCE TO RELATED APPLICATIONS

This application is a §371 national stage entry of International Application No. PCT/KR2008/005320, filed Sep. 10, 2008, which claims priority to Korean Patent Application No. 10-2007-0095940, filed Sep. 20, 2007, both of which are hereby incorporated by reference.

TECHNICAL FIELD

The present invention relates to a rechargeable type callus removal instrument for removing callus usually generated at soles and so on.

BACKGROUND ART

Generally, as we walk in shoes or keep out feet in contact with hard portions of shoes for a long time even in a stopped state, part of the foot skin turns hard, thereby forming calluses on the feet. Such calluses grow thicker as time goes, and in severe cases, they even split up. When the splitting occurs, it not only causes pains but may allow infiltration of germs through the split part, thereby causing infection.

In order to remove the calluses, a callus removing tool as shown in FIG. 12 has been widely used. To be more particular, referring to FIG. 12, a user removes calluses by holding a handle 200 and scrubbing off the calluses with a file plate 220 formed on either or both sides of a main body 210. However, since this type of conventional method requires the repetitive manual movements, the user easily gets tired to remove the calluses. Furthermore, the conventional callus removing tool is not hygienic because the calluses may scatter about in all directions, and also inappropriate for portable use due to inconvenience and an unpleasant look without a cover.

DISCLOSURE OF INVENTION

Technical Problem

Therefore, the present invention has been made in view of the above problems, and it is an object of the present invention to provide a callus removal instrument capable of removing calluses using a rotational force of a motor charged with electricity, improving portability thereof, and preventing entry of water to the inside, being improved in the structure of a file plate for contact with a foot surface and added with a hair removal function by a hair removal device attached to the file plate.

Technical Solution

In accordance with an aspect of the present invention, the above and other objects can be accomplished by the provision of a rechargeable type callus removal instrument comprising a main body having a flaring tube shape with one side opened; a plate fitted with an inner circumference of an opening of the main body, thereby covering the opening; a motor connected with an inner lower part of the plate through a fastening member and equipped with a motor shaft having a semicircular sectional shape; a callus storage fitted around the motor shaft of the motor and rotated in accordance with rotation of the motor shaft, thereby collecting calluses separated from a user's foot therein; a filing cap covering an upper surface of the callus storage and removing the calluses of the user's foot as rotating along with the callus storage in contact with a callus surface of the foot; a guide member inserted in an upper surface of the plate and protruded in a cylindrical shape, forming a barrier at a predetermined distance from outer circumferences of the callus storage and the filing cap, such that the calluses being removed by the filing cap are collected in the callus storage without scattering about to the outside; a recharging device mounted to a lower part of the motor; and an on/off device connected to the recharging device with one end thereof and to one side of the main body with the other end to control on and off states.

Advantageous Effects

In accordance with the above described rechargeable type callus removal instrument, callus removal can be achieved using a rotational force of a motor through electric recharging with an improved portability. In addition, infiltration of water into the callus removal instrument can be prevented. Since a plurality of triangular projections are formed on an upper surface of a filing cap contacting a foot surface, the callus removal efficiency can be greatly improved. Furthermore, by adding a hair removal device to the filing cap, a hair removal function can also be achieved.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a longitudinal sectional view of a rechargeable type callus removal instrument according to an embodiment of the present invention;

FIG. 2 is an exploded perspective view of the rechargeable type callus removal instrument according to the embodiment of the present invention;

FIG. 3 is a sectional view of a head part of the rechargeable type callus removal instrument out of operation;

FIG. 4 is a sectional view of the head part of the rechargeable type callus removal instrument in operation;

FIG. 5 is an exploded perspective view of a guide member of the rechargeable type callus removal instrument;

FIG. 6 is a perspective view of a callus storage of the rechargeable type callus removal instrument;

FIG. 7 is a perspective view of a bottom side of the callus storage of the rechargeable type callus removal instrument;

FIG. 8 is a plan view of a filing cap of the rechargeable type callus removal instrument, seen from above;

FIG. 9 is a sectional view of FIG. 8 cut along a line A-A;

FIG. 10 is a sectional view of a hair removal device mounted to an upper surface of the filing cap of the rechargeable type callus removal instrument;

FIG. 11 is a sectional view of another hair removal device applied to the upper surface of the filing cap of the rechargeable type callus removal instrument; and FIG. 12 is a perspective view of a conventional callus removal tool.

BEST MODE FOR CARRYING OUT THE INVENTION

FIG. 1 is a longitudinal sectional view of a rechargeable type callus removal instrument according to an embodiment of the present invention. FIG. 2 is an exploded perspective view of the rechargeable type callus removal instrument. FIG.

3 is a sectional view of a head part of the rechargeable type callus removal instrument out of operation. FIG. 4 is a sectional view of the head part of the rechargeable type callus removal instrument in operation. FIG. 5 is an exploded perspective view of a guide member of the rechargeable type callus removal instrument. FIG. 6 is a perspective view of a callus storage of the rechargeable type callus removal instrument. FIG. 7 is a bottom perspective view of the callus storage of the rechargeable type callus removal instrument. FIG. 8 is a plan view of a filing cap of the rechargeable type callus removal instrument, seen from above. FIG. 9 is a sectional view of FIG. 8 cut along a line A-A.

As shown in the drawings, the rechargeable type callus removal instrument according to the embodiment of the present invention comprises a main body 10 having a flaring tube shape with one side opened, a plate 20 fit with an inner circumference of the opening of the main body 10 thereby covering the opening, a motor 30 connected to an inner lower part of the plate 20 through a fastening member 99 and equipped with a motor shaft 31 having a semicircular sectional shape, a callus storage 40 fitted around the motor shaft 31 of the motor 30 and rotated along with the motor shaft 31, so as to store calluses removed from a user's foot, and a filing cap 50 covering an upper surface of the callus storage 40 to remove the callus as rotating together with the callus storage 40 in contact with a callus surface of the foot. The rechargeable type callus removal instrument further comprises a guide member 60 inserted in an upper surface of the plate 20 such that the callus being removed by the filing cap 50 can be collected in the callus storage 40 without scattering about to the outside. The guide member 60 is protruded in a cylindrical shape, thereby forming a barrier at a predetermined distance from outer circumferences of the callus storage 40 and the filing cap 50. In addition, the rechargeable type callus removal instrument comprises a recharging device 70 mounted to a lower part of the motor 30, and an on/off device 80 connected to the recharging device 70 with one end thereof and to one side of the main body 10 with the other end to control on and off states. The on/off device 80 includes a light emitting diode (LED) 83 to display a recharging state of a battery.

The plate 20 comprises a horizontal plate 21 in the form of a flat plate having a hole in the center, a lower flange 22 vertically protruded downward at an outer circumference of the horizontal plate 21, including a protrusion 22a on an outer circumference of a lower end of the horizontal plate 21, and an upper flange 23 protruded upward with respect to the horizontal plate 21.

The upper flange 23 includes an outer circumference fixing protrusion 23a disposed at an upper surface of the opening of the main body 10, a circular and an angular inner protrusion 23b and 23c formed at one side and the other side, respectively, of an inner circumference of an upper part of the outer circumference fixing protrusion 23a, and a fixing protrusion 23d formed at an outer circumference of an upper end thereof.

An O-ring 90 is inserted in a lower end of the outer circumference fixing protrusion 23a of the upper flange 23 of the plate 20. In addition, another O-ring 91 is inserted between a lower surface of the horizontal plate 21 of the plate 20 and an upper surface of the motor 30.

A cover member 100 is further comprised to cover the callus storage 40, the filing cap 50 and the guide member 60, being mounted in engagement with the fixing protrusion 23d protruded on the upper outer circumference of the upper flange 23 of the plate 20.

The callus storage 40 includes a cylindrical storage space 41 formed in the center, a partition 42 of a cylindrical shape disposed at a predetermined distance about the cylindrical storage space 41, and a plurality of storage spaces 43 sectioned in radial directions between the cylindrical storage space 41 and the cylindrical partition 42. Each corner of the storage spaces 43 is rounded to promote discharge of stored calluses. In addition, a fastening recess part 44 having a semicircular shape is protruded downward from a lower surface of the cylindrical storage space 41. The semicircular motor shaft 31 is inserted in the fastening recess part 44 to rotate the fastening recess part 44. Also, an elastic spring 45 is inserted in the fastening recess part 44. A flange is extended along the circumference of a lower end of the cylindrical partition 42, and a concave cut 46 is formed on the flange for engagement with a round fastener 53 of the filing cap 50.

At an inner lower end of the cylindrical storage space 41, a magnet 47 is mounted to generate magnetism operated to the motor shaft 31 of the motor 30.

The filing cap 50 covers upper surfaces of the cylindrical storage space 41 and the plurality of storage spaces 43 of the callus storage 40. A plurality of triangular protrusions 51 are formed upward on an upper surface of the filing cap 50. The triangular protrusions 51 are arranged at uniform intervals in a circumferential direction such that one vertex of each triangular protrusion 51 is directed to a rotational direction of the motor shaft 31.

More specifically, the triangular protrusions 51 comprise a plurality of concentric groups arranged with respect to the center of the upper surface of the filing cap 50. Additionally, a plurality of penetration holes 52 are formed in a circumferential direction at uniform distances from the center of the filing cap 50, such that the calluses being removed can be collected in the callus storage 40 through the penetration holes 52.

The guide member 60 comprises a first guide member 61 disposed at the upper surface of the plate 20, including a circular and an angular outer protrusion 61a and 61b formed on an outer circumference thereof for engagement with lower ends of the circular and the angular inner protrusions 23b and 23 of the plate 20. The guide member 60 further comprises an annular spring 62 mounted to an inner circumference of the first guide member 61, and a second guide member 63 moved up and down by elasticity of the annular spring 62. An upper fixing protrusion 61c of the first guide member 61 is inserted in a recess 63b formed on a lower flange 63a of the second guide member 63. The guide member 60 also can be fabricated one united body with a material having elasticity such as silicon or rubber, instead of a first guide member 61 and a second guide member 63.

The recharging device 70 comprises a rechargeable battery 71, a protector 72 covering an upper part of the rechargeable battery 71, a protection cover 73 enclosing both sides and a lower surface of the rechargeable battery 71, and a protection circuit 74 mounted between a lower part of the protector 72 and the upper part of the rechargeable battery 71, and connected to the on/off device 80 so as to stably maintain predetermined voltage and current, thereby preventing overloading and the like. In addition, an electrode 76 is further comprised, being protruded on the lower surface of the protection cover 73 downward with respect to the main body 10, with a rubber plate 75 interposed between the electrode 76 and the protection cover 73. The electrode 76 is inserted in a power line (not shown) to enable recharging of power.

The electrode 76 is embedded in an insulator medium 77 which is connected by the fastening member 99. In addition, an O-ring 77a is inserted between an inner surface of a lower end of the main body 10 and a lower surface of a flange part of the insulator medium 77 to prevent entry of water to the inside of the callus removal instrument.

The on/off device 80 comprises a circuit board 81 attached to an inner side surface of the main body 10 to control the operations of the motor 30, the protection circuit 74 and the electrode 76, a switch 82 controlling on and off states of the callus removal instrument, an LED 83 radiating under the control of the circuit board 81 when the battery 71 is recharged, a first protection plate 84 covering the switch 82 and the LED 83, and a second protection plate 85 protecting the first protection plate 84.

FIG. 10 is a sectional view wherein a hair removal device is added to the upper surface of the filing cap 50 of the rechargeable type callus removal instrument according to the embodiment of the present invention. FIG. 11 is a sectional view showing another hair removal device attached to the upper surface of the filing cap 50.

As shown in FIG. 10, a hair removal device 110 having a hair removal function is mounted to the upper surface of the filing cap 50. The hair removal device 110 comprises a double-sided adhesive sticker 111 covering the whole upper surface of the filing cap 50, an elastic medium 112 attached to an upper surface of the double-sided adhesive sticker 111, and a polisher 113 attached to an upper surface of the elastic medium 112 through the medium of the double-sided adhesive sticker 111.

Here, the elastic medium 112 is formed of a material having predetermined elasticity, such as sponge.

The hair removal device 120 as shown in FIG. 11 comprises a rubber magnet 121 attached by magnetism to cover the whole upper surface of the filing cap 50, the double-sided adhesive sticker 111 attached to the upper surface of the rubber magnet 121, and the polisher 113 attached to an upper surface of the double-sided adhesive sticker 111.

With the above described component parts, the rechargeable type callus removal instrument is structured as follows. The recharging device 70 is mounted through the opening of the main body 10 to be connected with the on/off device 80. The motor 30 is mounted to an upper part of the recharging device 70. The horizontal plate 21 of the plate 20 is fixed to an upper surface of the motor 30 by the fastening member 99. The motor shaft 31 of the motor 30, being protruded upward through the center of the horizontal plate 21 of the plate 20, is inserted in the center of the guide member 60. The circular and the angular outer protrusions 61a and 61b formed at both lower ends of the first guide member 61 are engaged with the circular and the angular inner protrusions 23b and 23c of the plate 20, respectively. In this state, the annular spring 62 is inserted to fit with the inner circumference of the first guide member 61, and the second guide member 63 is inserted to be disposed on the annular spring 62. More specifically, as the upper end fixing protrusion 61c of the first guide member 61 is inserted in the recess 63b formed on the lower flange 63a of the second guide member 63 and then rotated, the upper end fixing protrusion 61c is engaged with an upper surface of the lower flange 63a of the second guide member 63 inseparably. The cover member 100 is separably fastened to the fixing protrusion 23d of the plate 20.

When the motor shaft 31 is insertedly mounted in the fastening recess part 44 having a semicircular shape protruded downward from the lower surface of the cylindrical storage space 41, the insertion state of the motor shaft 31 is maintained due to magnetism of the magnet 47 mounted to the inner lower end of the cylindrical storage space 41. The filing cap 50 covers the upper surface of the protrusion storage 40. More particularly, a pair of the round fasteners 53 protruded downward on the filing cap 50 are inserted in the concave cuts 46 formed at the flange of the protrusion storage 40 and rotated by a predetermined angle. Therefore, the round fasteners 53 are engaged with the lower surface of the flange.

When the user wants to remove calluses from his or her foot using the rechargeable type callus removal instrument, the motor 30 is first driven by applying power to the on/off device 80. Then, the protrusion storage 40 connected with the motor shaft 31 is rotated and according to this, the triangular protrusions 51 formed on the upper surface of the filing cap 50 remove the calluses from the user's foot. The calluses being removed by the filing cap 50 are collected in the storage spaces 43 of the callus storage 40 through the plurality of penetration holes 52, not being discharged to the outside by the second guide member 63.

In order to throw away the calluses collected in the storage spaces 43 of the callus storage 40, the filing cap 50 is rotated in the opposite direction to a fastening direction until the round fastener 53 is corresponded to the concave cut 46 of the flange of the callus storage 40. Then, the filing cap 50 can be separated upward and the collected calluses can be thrown away.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. A rechargeable type callus removal instrument comprising:
    a main body having a flaring tube shape with one side opened;
    a plate fitted with an inner circumference of an opening of the main body, thereby covering the opening;
    a motor connected with an inner lower part of the plate through a fastening member and equipped with a motor shaft having a semicircular sectional shape;
    a callus storage fitted around the motor shaft of the motor and rotated in accordance with rotation of the motor shaft, thereby collecting calluses separated from a user's foot therein;
    a filing cap covering an upper surface of the callus storage and removing the calluses of the user's foot as rotating along with the callus storage in contact with a callus surface of the foot;
    a guide member inserted in an upper surface of the plate and protruded in a cylindrical shape, forming a barrier at a predetermined distance from outer circumferences of the callus storage and the filing cap, such that the calluses being removed by the filing cap are collected in the callus storage without scattering about to the outside;
    a recharging device mounted to a lower part of the motor;
    an on/off device connected to the recharging device with one end thereof and to one side of the main body with the other end to control on and off states; wherein the recharging device comprises: a rechargeable battery; a protector covering an upper part of the rechargeable battery; a protection cover covering both sides and a lower surface of the rechargeable battery; a protection circuit mounted between a lower part of the protector and the upper part of the rechargeable battery, and connected to the on/off device so as to stably maintain predetermined voltage and current, thereby preventing overloading and the like; and an electrode protruded on the lower surface of tile protection cover downward with respect to the main body, with a rubber plate interposed between the electrode and the protection cover, and inserted in a power line to achieve recharging of power;

wherein the electrode is embedded in an insulator medium connected by a fastening member, and an O-ring is inserted between an inner surface of a lower end of the main body and a lower surface of a flange part of the insulator medium so as to prevent entry of water.

2. The rechargeable type callus removal instrument according to claim 1, wherein the plate comprises:
   a horizontal plate in the form of a flat plate having a hole in the center;
   a lower flange vertically protruding downward at an outer circumference of the horizontal plate and including a protrusion formed on an outer circumference of a lower end of the horizontal plate; and
   an upper flange protruded upward with respect to the horizontal plate.

3. The rechargeable type callus removal instrument according to claim 2, wherein the upper flange comprises:
   an outer circumference fixing protrusion disposed at an upper surface of the opening of the main body;
   a circular and an angular inner protrusion formed at one side and the other side, respectively, of an inner circumference of an upper part of the outer circumference fixing protrusion; and
   a fixing protrusion formed at an outer circumference thereof.

4. The rechargeable type callus removal instrument according to claim 3, wherein O-rings are inserted in a lower end surface of the outer circumference fixing protrusion of the upper flange of the plate, and between a lower surface of the horizontal plate of the plate and an upper surface of the motor.

5. The rechargeable type callus removal instrument according to claim 3, further comprising a cover member mounted in engagement with the fixing protrusion formed on the upper outer circumference of the upper flange of the plate to cover the callus storage, the filing cap and the guide member.

6. The rechargeable type callus removal instrument according to claim 3, wherein the guide member comprises:
   a first guide member disposed at the upper surface of the plate, including a circular and an angular outer protrusion formed on an outer circumference thereof for engagement with lower ends of the circular and the angular inner protrusions of the plate, and an upper fixing protrusion;
   an annular spring mounted to an inner circumference of the first guide member; and
   a second guide member moved up and down by elasticity of the annular spring, including a recess formed on a lower flange thereof to receive the upper fixing protrusion of the first guide member.

7. The rechargeable type callus removal instrument according to claim 6, the guide member comprises one united body with a member having elasticity, instead of a first guide member, a spring and a second guide member.

8. The rechargeable type callus removal instrument according to claim 1, wherein the callus storage comprises:
   a cylindrical storage space formed in the center thereof;
   a cylindrical partition formed in a cylindrical shape and disposed at a predetermined distance about the cylindrical storage space;
   a plurality of storage spaces sectioned in radial directions between the cylindrical storage space and the cylindrical partition such that each corner of which is rounded;
   a fastening recess part having a semicircular shape protruded downward from a lower surface of the cylindrical storage space such that the semicircular motor shaft is inserted in the fastening recess part to rotate the fastening recess part; and
   a concave cut formed on a flange, which is extended along a lower circumference of the cylindrical partition, for engagement with a round fastener of the filing cap.

9. The rechargeable type callus removal instrument according to claim 8, further comprising:
   an elastic spring inserted in the semicircular fastening recess part; and
   a magnet insertedly mounted at an inner lower end of the cylindrical storage space to generate magnetism operated to the motor shaft of the motor.

10. The rechargeable type callus removal instrument according to claim 8, wherein the filing cap covers an upper surface of the cylindrical storage space and the plurality of storage spaces, and comprises:
   a plurality of triangular protrusions formed upward on an upper surface of the filing cap, the triangular protrusions being arranged at uniform intervals in a circumferential direction such that one vertex of each triangular protrusion is directed to a rotational direction of the motor shaft, and constituted by a plurality of concentric groups arranged with respect to the center of the upper surface of the filing cap, and
   a plurality of penetration holes formed in a circumferential direction at uniform distances from the center of the filing cap, such that the calluses being removed can be collected in the callus storage through the penetration holes.

11. The rechargeable type callus removal instrument according to claim 1, wherein the on/off device comprises:
   a circuit board attached to an inner side surface of the main body to control the operations of the motor, the protection circuit, a light emitting diode (LED) and the electrode;
   a switch controlling on and off states of the callus removal instrument;
   a first protection plate covering the switch and the LED; and
   a second protection plate protecting the first protection plate.

12. The rechargeable type callus removal instrument according to claim 1, wherein a hair removal device having a hair removal function, is further mounted to an upper surface of the filing cap, the hair removal device comprising:
   a double-sided adhesive sticker covering the whole upper surface of the filing cap;
   an elastic medium attached to an upper surface of the double-sided adhesive sticker; and
   a polisher attached to an upper surface of the elastic medium through the medium of the double-sided adhesive sticker.

13. The rechargeable type callus removal instrument according to claim 1, wherein a hair removal device having a hair removal function, is further mounted to an upper surface of the filing cap, the hair removal device comprising:
   a rubber magnet attached by magnetism to cover the whole upper surface of the filing cap;
   a double-sided adhesive sticker attached to the upper surface of the rubber magnet; and
   a polisher attached to an upper surface of the double-sided adhesive sticker.

14. The rechargeable type callus removal instrument according to claim 1, further comprising a polisher having a hair removal function, being attached to an upper surface of the filing cap by an adhesive sticker.

* * * * *